United States Patent [19]

Rickards

[11] Patent Number: 4,527,568

[45] Date of Patent: Jul. 9, 1985

[54] DUAL CHAMBER PACER WITH ALTERNATIVE RATE ADAPTIVE MEANS AND METHOD

[75] Inventor: Anthony F. Rickards, London, England

[73] Assignee: Vitafin N.V., Curacao, Netherlands Antilles

[21] Appl. No.: 566,101

[22] Filed: Dec. 27, 1983

[51] Int. Cl.³ .............................................. A61N 1/36
[52] U.S. Cl. ............................................. 128/419 PG
[58] Field of Search ................................ 128/419 PG

[56] References Cited

U.S. PATENT DOCUMENTS

| | | | |
|---|---|---|---|
| 3,593,718 | 7/1971 | Krasner | 128/419 PG |
| 3,921,642 | 11/1975 | Preston et al. | 128/419 PG |
| 4,228,803 | 10/1980 | Rickards | 128/419 PG |
| 4,284,082 | 8/1981 | Funke et al. | 128/419 PG |
| 4,298,007 | 11/1981 | Wright et al. | 128/419 PG |
| 4,305,396 | 12/1981 | Wittkampf et al. | 128/419 PG |
| 4,333,470 | 6/1982 | Barthel | 128/419 PG |
| 4,373,531 | 2/1983 | Wittkampf et al. | 128/419 PG |
| 4,467,807 | 8/1984 | Bornzin | 128/419 PG |
| 4,467,810 | 8/1984 | Vollmann | 128/419 PG |

OTHER PUBLICATIONS

Geddes et al., "The Exercise-Responsive Cardiac Pacemaker", *IEEE Trans Biomed Eng.*, vol. BME-31, No. 12, Dec. 1984, pp. 763–770.

"Rate Responsive Pacing", by Anthony F. Rickards et al., Clin. Prog. Pacing and Electrophysiol., vol. 1, No. 1, 1983.

"AV Synchrony and Cardiac Rate", by Seymour Furman, M.D., Pace, vol. 6, May–Jun. 1983, Part I.

"The Use of QT Interval to Determine Pacing Rate: Early Clinical Experience", by A. F. Rickards et al., Pace, vol. 6, Mar.–Apr. 1983, Part III.

*Primary Examiner*—William E. Kamm
*Assistant Examiner*—Mitchell J. Shein
*Attorney, Agent, or Firm*—Woodcock Washburn Kurtz Mackiewicz & Norris

[57] ABSTRACT

A dual chamber pacemaker system is disclosed with means for operating in one or another of alternate rate adaptive modes. The pacemaker incorporates an atrial synchronous mode, wherein, pacing rate is determined as a function of sensed atrial signals. It also incorporates a $T_x$ mode, wherein pacing rate is controlled by a sensed QT interval, and an extra sensor mode, wherein pacing rate is controlled as a function of at least one sensed body parameter. The pacemaker comprises means for automatically testing the applicability or appropriateness of the mode currently in use, and for automatically selecting the appropriate rate control mode.

21 Claims, 4 Drawing Figures

DUAL CHAMBER PACER WITH ALTERNATIVE RATE ADAPTIVE MEANS AND METHOD

BACKGROUND OF THE INVENTION

This invention relates to pacemaker systems and the use thereof, and in particular pacemaker systems which are automatically rate adaptable.

The use and employment of rate adaptive or physiological pacemakers is now gaining an increasing acceptance, although it has been slow coming. The principle of using atrial activity to trigger ventricular pacing has been implemented in implantable devices for about two decades, but even to date such pacemakers are very much in the minority. However, the reasons for the historical limited acceptance of atrial synchronous pacemakers, and other types of dual chamber pacemakers, are being overcome by the industry. The problems with reliable sensing of atrial activity, bulky short-lived generators and ventricular competitive pacing are being solved in varying degrees.

A clear understanding of the factors responsible for the adjustment of cardiac output in relation to metabolic needs, and interest in sensing arrangements other than the atrium to provide physiological information, has contributed to evoking technical development in this area. In short, the object is to define a pacing system able to confer physiological benefit under a wide variety of conditions and cardiac rhythms. The ability to adjust cardiac output in relation to metabolic needs is a fundamental property of the intact cardiovascular system, and increase of heart rate alone can increment cardiac output by 300 percent in normal adults; combined with stroke volumne increases of around 50 percent this produces the normal 4 to 5 - fold increase of cardiac output found in exercise. In patients with complete heart block the loss of rate control thus has a profound effect on exercise haemodynamics. Thus, loss of rate control applies not only to patients with atrioventricular disociation, but also to subjects with an abnormal sinus response to exercise, even though atrial synchrony may be maintained.

Two main approaches currently exist in the design of physiologically adaptive pacemakers. The first is the dual chamber pacemaker, e.g. use of atrial synchronous ventricular pacing. If the atrium is normally responsive to metabolic demands, this pacing system represents the ideal pacing modality. Such a pacing system has the advantage that it not only provides rate control mediated by the sinus node, but also allows physiological A-V synchrony to be maintained. The haemodynamic benefit of dual chamber devices (including VDD and DDD) has been established both in the long and short term, and the use of such in patients with predominated or exercise-induced high grade A-V block and normal sinus function is clearly mandated.

There remain, however, some technical problems related to the use of atrial synchronous pacemakers. The incidence of pacemaker mediated tachycardia is a problem that the industry has been working on vigorously. One of the predominant problems that must be solved in this area is that of achieving the ability to sense the difference between physiological and pathological atrial tachycardias.

At the present time it is estimated that over half the patients receiving implanted cardiac pacemakers have abnormal atrial functions. Primary sino-atrial disease is present in 48% of patients presenting for pacing in the U.S., and many of the remaining patients will have associated sino-atrial disease, or will develop atrial arhythmias during the course of their life. Thus, perhaps less than ⅓ of prospective patients with symptomatic bradycardia have a normal sinus node which can be used as a faithful determinant of metabolic demand.

The above considerations have stimulated interest in a second approach to the design of physiologically adaptive pacemakers. Such second approach system produces changes in the ventricular rate by using other means of sensing metabolic demand or exercise itself, independent of atrial activity. Ventricular pacing systems now in development have been based on varying principles. The QT sensitive pacemaker responds to an indication of metabolic demand and therefore is sensitive to the effects of emotion and those cardioactive drugs which alter the catecholamine sensitivity of the heart. Reference is made to U.S. Pat. Nos. 4,228,803, Rickards, and 4,305,396, Wittkampf et al, which describe embodiments of a evoked QT sensing type pacemaker. A pacemaker using the basic evoked QT sensing arrangement has been developed by the assignee of this application, and is hereinafter referred to as operating in the $T_x$ mode. The advantages of this system include its inability to induce pacemaker mediated tachycardias. Of course, it does not provide suitably timed atrial contraction.

In addition to the $T_x$ mode rate adaptive pacer, other systems are under development which use body sensors for monitoring different body parameters, the pacemaker having means for controlling and adapting rate as a function of the sensed body parameter. Such systems include sensors for pH control, control by central venus oxygen content, temperature control, and resperation rate control. Reference is made to the paper titled "Rate Responsive Pacing", Rickards et al, Vol. 1, No. 1, 1983, Clin. Prog. Pacing and Electrophysiol.

SUMMARY OF THE INVENTION

It is the primary object of this invention to provide a dual chamber pacemaker with the capability of offering alternative rate adaptive modes of operation.

It is another object of this invention to provide a pacing system which presents the major advantages of the prior art atrial synchronous type pacemaker but which is automatically adaptive to at least one alternate rate adaptive mode if the atrial synchronous mode is found to be inappropriate.

It is another object of this invention to provide a dual chamber pacemaker which additionally has QT means for determining the desired ventricular pacing rate.

It is another object of this invention to provide a pacemaker system comprising means for atrial synchronous operation, having the further facility of determining when the atrial rate indication is no longer reliable and for switching to an alternate mode of rate adaptive pacing.

It is another object of this invention to provide a dual chamber pacemaker, and method of operation thereof, for operating in a DVI mode of operation and comprising nonatrial means for controlling the rate of delivered pacing pulses.

It is another object of this invention to provide a highly flexible and reliable rate adaptive pacemaker which gives the user the option of a plurality of rate adaptive modes, including an atrial controlled mode, with means for automatically selecting the desired rate control mode and additional means for externally programming the desired rate adaptive mode.

In view of the above objects, there is provided a dual chamber pacemaker system comprising atrial control means for controlling the pacing rate as a function of sensed atrial signals, e.g. atrial synchronous pacing, in combination with alternate rate control means such as QT sensing or body parameter sensing for alternate controlling of the pacing rate, and automatic means for determining when the pacing rate is to be atrial controlled and when alternate rate controlled.

DESCRIPTION OF THE PREFERRED EMBODIMENTS

Figures 1, 4:
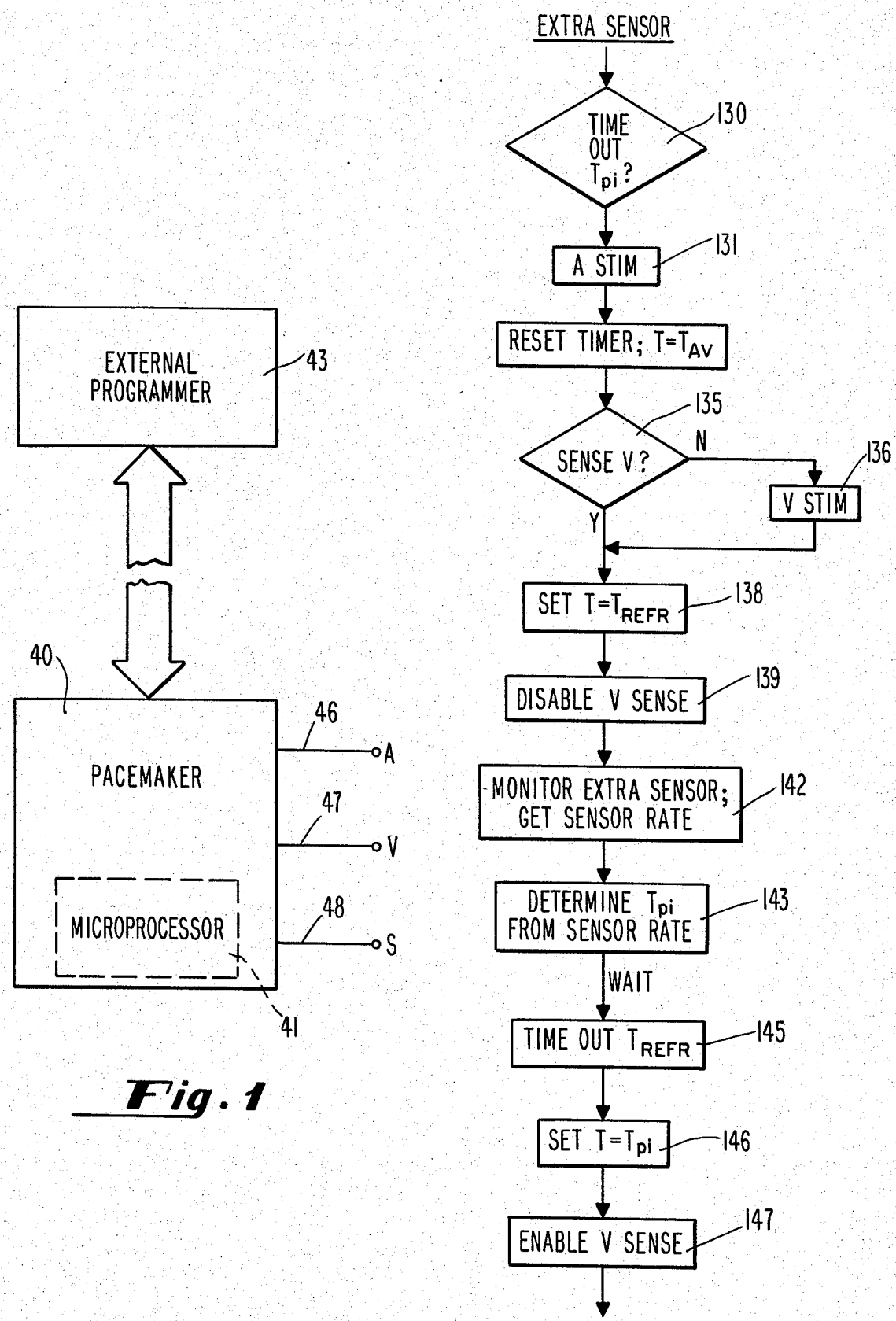
FIG. 1 is a block diagram illustrating a pacemaker as used in this invention, having dual chamber terminals and at least one additional body sensor, the pacemaker being in communication with an external programmer.
FIG. 4 is a flow diagram of a microprocessor routine for operating the pacemaker of this invention in an extra sensor mode of rate adaptive operation.

In discussing the pacemaker system of this invention, reference is made to the prior art which teaches the use of microprocessor capability in an implanted pacemaker, as well as the art of external programmer communication with an implanted pacemaker. Reference is made to U.S. Pat. Nos. 4,228,803, 4,305,396, describing operation of embodiments of a $T_x$ pacemaker, which patents are incorporated herein by reference. Pending U.S. application Ser. Nos. 436,411, 465,890 and 465,891, assigned to the same assignee, disclose embodiments of a microprocessor implantable pacemaker and means for communication between the implanted pacemaker and external programmer means, and are also incorporated by reference. The prior art, including the referenced patents and applications, teaches and discloses the use and means of use of a microprocessor in controlling the operation of an implanted pacemaker. Accordingly, the specification does not contain a detailed description of the techniques of programming a microprocessor, storing data in memory and retrieving it, carrying out such operations as timing time intervals and setting up sensing windows, etc. These operations are well known in the art and are taught by the above references as well as by other published patents and articles dealing with this area. However, in order to facilitate understanding of the invention, certain variables, terms and operations are defined as follows.

A sense—this refers to sensing a natural atrial signal (P wave). Thus, enabling the A sense refers to enabling the sensing of a P wave through the A sense detection circuitry.

V sense—this refers to sensing a natural ventricular signal (QRS); enabling V sense refers to enabling the V sense detection circuitry.

$T_{AV}$—The AV time delay between an atrial signal (sensed or delivered) and the following ventricular stimulus.

$T_{AA}$—The pacing cycle, from atrial event (natural or delivered stimulus) to next atrial event.

Overdrive—The technique of setting the pacing interval to overdrive the natural rate, so that a stimulus is delivered instead of inhibiting stimulus delivery.

$T_{refr}$—The refractory interval time.

Extra sensor—This refers to any body parameter sensor or means of sensing a body parameter. For example, this may include means for sensing pH, venus oxygen content, body temperature, respiration rate, etc.

Sensor rate—an indicated pacing rate derived from sensor data.

$T_{pi}$—The time interval corresponding to one pacing cycle, i.e., $T_{AA}$ between two delivered atrial stimulus pulses.

DVI—The sequential mode of dual chamber pacing, characterized by pacing in both the atrium and the ventricle (D); sensing in the ventricle (V); and inhibiting (I) in response to a natural ventricular signal.

$T_x$—The mode of rate control wherein rate information is obtained by determining the time interval between a delivered stimulus and the evoked QRS.

$A_{stim}$—A delivered atrial stimulus.

$V_{stim}$—Delivered ventricular stimulus.

Timer—The microprocessor controlled timer means for timing elapsed time since the start of the pacemaker cycle.

Set T—The step of setting a time T which, when reached by the timer, will initiate a microprocessor timeout response.

T sense window—The period of time spanning both sides of the expected evoked T wave signal during which the pacemaker looks for an evoked T wave.

Q-T—The interval between a delivered ventricular stimulus and an evoked T wave.

Sync mode—Atrial synchronous mode of pacemaker operation.

Referring now to FIG. 1, there is shown a simple block diagram illustrating the primary components of the system. A pacemaker 40 is illustrated, which contains therein a microprocessor 41. The microprocessor controls pacemaker activity as set forth in referenced application Ser. Nos. 436,411 and 465,890. The pacemaker is in two way communication with external programmer apparatus 43, which may be of the type as described in referenced U.S. application Ser. No. 465,891. The pacemaker communicates through lead 46 with atrial terminal or terminals A, for sensing and/or pacing in the atrium. The atrial lead may be either unipolar or bipolar. Similarly, lead 47 connects the pacer with the patient's ventricle, for either unipolar or bipolar pacing and/or sensing. A third lead 48 is illustrated as connecting the pacer with a sensor designated S, which is suitably a body parameter sensor of the type described. It is to be understood that S may represent one or more different types of body parameter sensors or sensing means.

Figure 2:
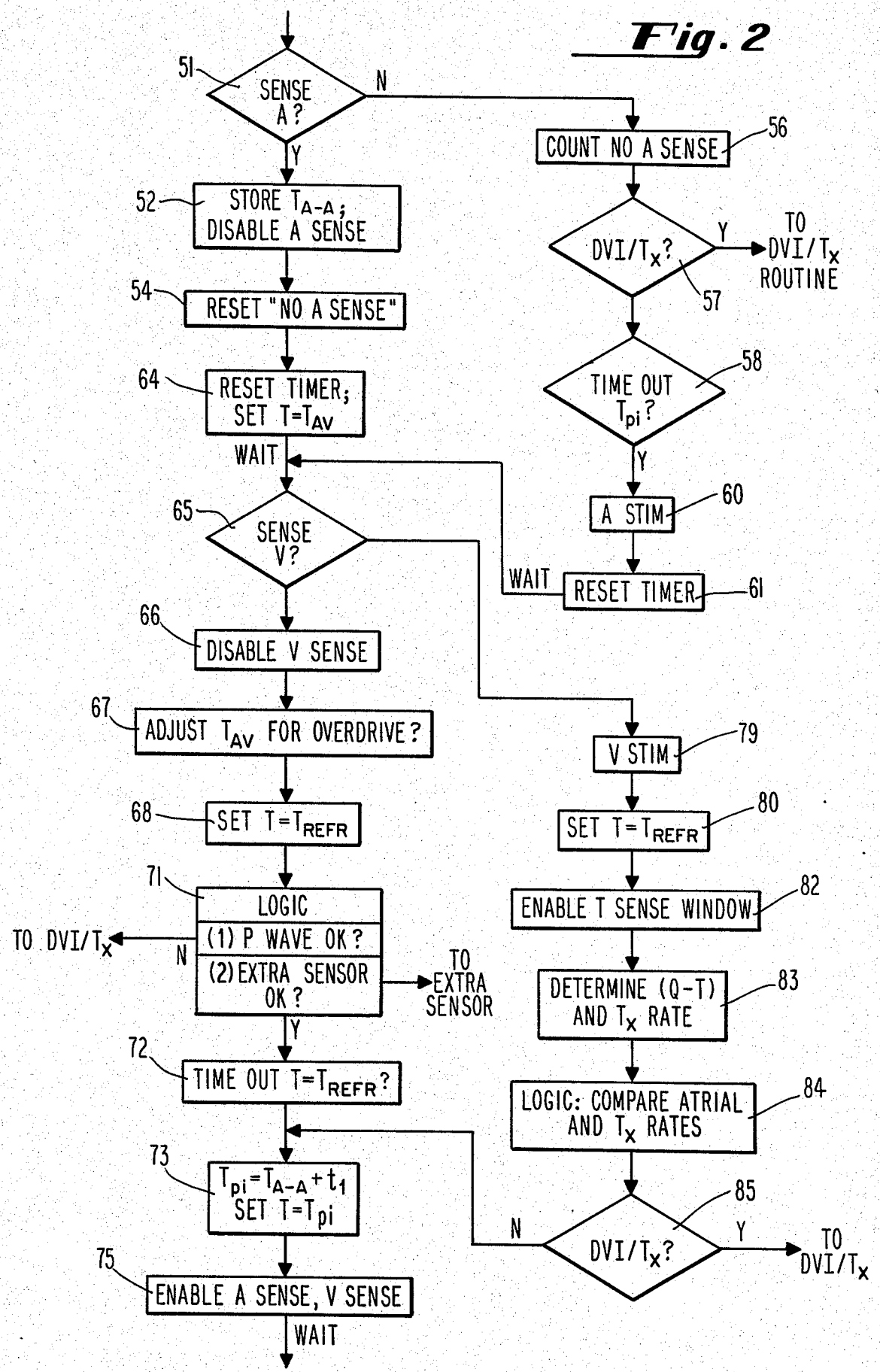
FIG. 2 is a flow diagram of a microprocessor subroutine for operating the pacemaker of this invention in an atrial synchronous mode, with determining means for determining whether the pacemaker should switch to another mode of rate control.
Figure 3:
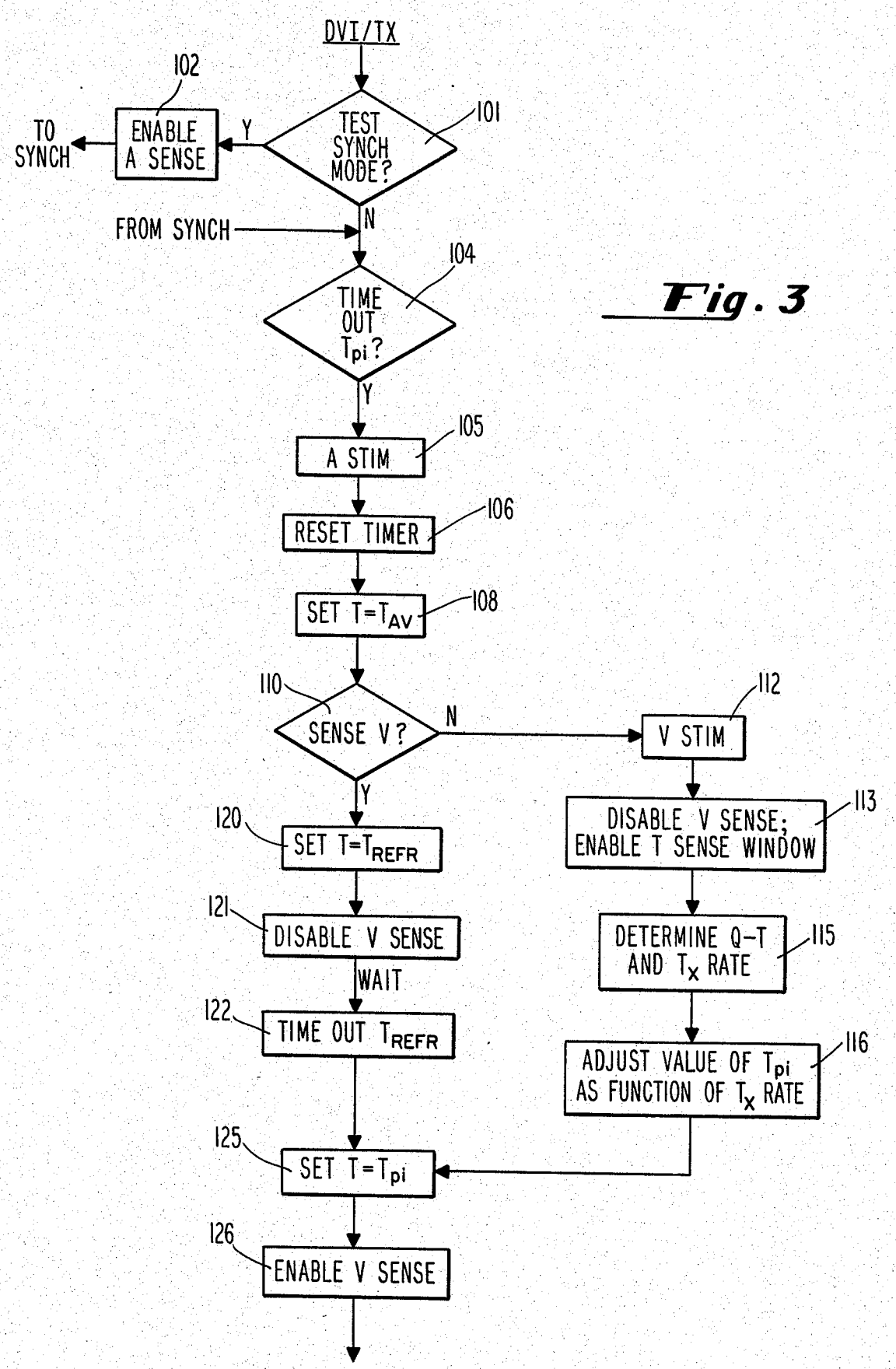
FIG. 3 is a flow diagram of a microprocessor routine for operating the pacemaker of this invention in a $DVI/T_x$ rate adaptive mode of operation.

Three microprocessor rate control flow paths are shown in FIGS. 2, 3 and 4. FIG. 2 shows a flow diagram which controls operation when the pacing rate is being derived from the sensed atrial signals. FIG. 3 illustrates a $DVI/T_x$ mode which incorporates $T_x$ control. And FIG. 4 illustrates an extra sensor mode which covers control by one or more extra body sensors. In each of these flow diagrams the steps material to the invention are included, while steps unnecessary for the purpose of illustrating the invention are omitted.

Referring to FIG. 2, which is called the synch path, the starting point is understood to be the end of one atrial cycle and the beginning of the next. The first block 51 represents a determination of whether an atrial signal has been sensed, or whether there has been a time out of the pacing interval. An A sense flag is set or not, depending upon this determination. If yes, meaning an atrial signal has been sensed, the cycle time $T_{A-A}$ is stored and the A sense circuitry is disabled at 52. The "No A sense" counter is reset to zero at block 54. At block 64 the timer is set to zero, indicating the start of timing of a new cycle; the time T is set to the AV delay time $T_{AV}$ and the pacemaker waits to see whether the AV delay times out or whether a natural ventricular QRS is sensed. If a natural QRS is sensed at block 65, the program proceeds at block 66 to disable V sense. If no natural QRS is sensed, meaning the AV delay timed out, the program branches to the right for delivery of a ventricular stimulus at block 79.

If, at block 51 no atrial wave (P) is sensed, the program branches to block 56 and increments the "No A sense" counter. The count of successive failures to sense a P wave is done so that if a predetermined number of atrial signals are missed, the pacemaker is caused to switch to $T_x$ rate control. At block 57, the pacemaker examines the count, and determines whether to stay with the synchronous mode of operation, or branch to the DVI/$T_x$ routine. For example, the decision to branch may be programmed to occur when the No A sense count reaches 10. Assuming that it stays in the synchronous mode, the pacemaker next confirms a time out of the pacing interval $T_{pi}$ at 58, and delivers an atrial stimulus at 60. The timer is reset to zero at 61, starting a new cycle. The pacemaker then branches to the "sense V?" block 65 and waits.

Assuming that a QRS has been sensed at block 65, the V sense is disabled at block 66 and the program then proceeds at block 67 to determine whether to adjust $T_{AV}$ for overdrive, i.e., make the AV delay shorter. The effect of a shorter AV delay is to promote pacing of the ventricle earlier than the anticipated natural QRS, so as to enable the measurement of a Q-T interval and get a $T_x$ rate evaluation. In the case of a delivered atrial stimulus, which is known to the pacer becasue the sense A flag was reset at block 51, the pacer may automatically set $T = T_{AV} - t_2$. The value of $t_2$ is a small value designed to decrease the AV delay in order to attempt to override the natural QRS. Alternately, if a natural P wave was sensed, causing setting of the sense A flag at block 51, the pacemaker microprocessor may be programmed to periodically decrease the value of $T_{AV}$, e.g., every 10 or 100 pacer cycles, so as to obtain a Q-T measurement. The programming of the pacemaker for adjustment of $T_{AV}$ for overdrive is a matter of operator judgment, and may be controlled by external programming of the implanted pacemaker. In another arrangement, the pacemaker may adjust $T_{AV}$ for overdrive as part of the operation at block 61, in order to more vigorously ensure a QT determination immediately following the absence of a natural P wave.

Next, at block 68 the time T is set to the refractory period, and at block 71 a logic analysis is performed during the time that the microprocessor waits for the time out of the refractory period. At this time, data on the sensed P waves may be analyzed, to determine whether the atrial rate is appropriate. If not, the pacer branches to the appropriate point in the DVI/$T_x$ path. Alternately, or in addition, the pacer may check data from the extra body sensor or sensors, and make a similar analysis. If the sensor analysis indicates that atrial rate control is inappropriate, the pacer branches to the appropriate block of the extra sensor loop. Assuming that atrial control is maintained, the pacemaker waits for time out of the refractory period at block 72. At block 73, pacing interval is then set equal to the last sensed cycle length ($T_{A-A}$) plus $t_1$, where $t_1$ is a small value. Thus, the pacing rate tracks the natural rate with some hysteresis, and T is set to the new $T_{pi}$. As is known in the art, the setting of the pacing rate is subject to maximum and minimum limitations, not shown. Also, the algorithm of block 73 suitably limits the change in pacing rate from cycle to cycle, providing a "fly wheel" effect in a known manner. The A sense and V sense circuits are then enabled at block 75, and the program waits for the next cycle to start at block 51.

Still referring to the synch program of FIG. 2, if no natural ventricular QRS is sensed at 65, meaning that the AV interval has timed out, a V stimulus is delivered at 79 and the time thereof is stored, and T is set equal to the refractory period at 80. The T wave sense window is enabled at 82, for sensing an evoked T wave during a predetermined window of time. At block 83 the pacemaker senses the evoked T wave and determines the QT interval and desirable $T_x$ rate. At block 84 the microprocessor compares the atrial and $T_x$ rates, and determines whether it is appropriate to maintain atrial control or switch to $T_x$ control. This comparison may comprise simply comparing the difference of the atrial and $T_x$ determined rates to a predetermined value, or may comprise a more complex algorithm. If it is determined appropriate to switch, the pacer branches to the appropriate point in the DVI/$T_x$ loop. If atrial control is to be maintained, pacing rate is set at block 73 and A sense and V sense are enabled at block 75.

Referring now to FIG. 3 which illustrates the DVI/$T_x$ sub-routine, at block 101 the pacemaker checks to see whether it is desired to test the synchronous mode. This feature is utilized so that the pacemaker can be programmed to return to the normal dual chamber atrial rate controlled mode of operation, if this is appropriate. For example, the mode switch can be made after 100 or 1000 pacer cycles. If the pacer does call for transfer to the synchronous mode, A sense is enabled at block 102, and the pacer proceeds to block 51 of the synch routine. If not, the pacemaker waits for time out of the pacing interval at 104 and then delivers an atrial stimulus at 105. The timer is then reset to zero at 106 for the start of the new cycle, and the time T is set equal to $T_{AV}$ at 108. If, at block 110, a natural ventricular signal is sensed, the pacer sets T to the refractory period at block 120 and disables V sense at 121. Upon time out of the refractory period, T is set to the pacing interval at 125, and V sense is enabled at 126. Following this, the pacer loops back to block 101. Note that for this loop, there is no atrial sense, since the pacemaker is operating in the DVI mode subject to the $T_x$ rate control, i.e., DVI/$T_x$.

Returning to the V sense block 110, if there is no QRS sensed, then a ventricular stimulus is delivered at 112. The time of the delivered $V_{stim}$ is recorded, for the purpose of determining the QT interval. Following this, V sense is disabled and the T sense window is enabled at 113. The evoked T wave is sensed, the QT interval is measured and the indicated $T_x$ rate is determined at block 115. Following this, at block 116 the pacing interval $T_{pi}$ is set as a function of the $T_x$ rate. The algorithm of block 116 limits the change in rate for any given cycles so as to ensure a gradual change in rate when, for example, control has been passed from atrial to $T_x$. The program then sets $T_{pi}$ to the timer, enables V sense and exists.

Referring now to the extra sensor loop, as illustrated in FIG. 4, at the beginning of the loop there may be an opportunity to transfer to synchronous mode, as discussed in connection with block 101 of FIG. 3. Assuming no transfer, at block 130 it is determined whether $T_{pi}$ has timed out. Assuming yes, the atrial stimulus is delivered at 131, following which at block 133 the timing cycle is restarted by setting the timer to zero and T is set equal to $T_{AV}$. At block 135, if no QRS is sensed within the AV interval, a ventricular stimulus is delivered at block 136. If a QRS is sensed, the pacemaker proceeds directly to set T equal to the refractory period at block 138 and disables V sense at block 139. The extra sensor is monitored at block 142, and the pacing rate as indicated by the sensor information is determined. A conventional technique for translating sensor data into an indicated pacing rate may be used. Based on the sensor-determined pacing rate, a modified $T_{pi}$ is set at block 143. When the refractory period is timed out at block 145, T is set equal to $T_{pi}$ at block 146 and V sense is enabled at block 147, whereupon the program exists and returns to the start.

It is within the scope of this invention to provide, through external programming, for enabling or disabling branching from one mode of operation to the other. For example, if it is desired to prohibit any mode of operation but synchronous operation, then blocks 57, 71 and 85 of FIG. 2 are bypassed. This change can be made by program signals transmitted from external source 43, in a well known and conventional manner. Likewise, block 101 of FIG. 3, or a corresponding block (not shown) in the extra sensor routine of FIG. 4, may be bypassed, so as to maintain operation in either the $DVI/T_x$ mode or the extra sensor mode. Thus, any degree of automatic switching from one mode to another may be achieved or programmed. It is to be understood that when the pacer branches from the synchronous mode to the $DVI/T_x$ or extra sensor mode, the A sense is preferably disabled as part of the switching routine.

I claim:

1. A dual chamber pacemaker, having means for sensing atrial heartbeat signals and means for sensing ventricular heartbeat signals, and means for delivering stimulus pulses at least to the ventricle, comprising:
   atrial rate means for determining the rate of said sensed atrial signals,
   QT means for sensing the ventricular QT interval and for determining an indicated pacing rate therefrom,
   comparison means for making a comparison of said indicated rate with the rate of sensed atrial heartbeat signals, and
   control means for controlling the timing of said pacemaker as a function of said indicated rate or as a function of sensed atrial signals depending upon said comparison.

2. The pacemaker as described in claim 1, comprising means for determining if a sensed atrial signal is absent for a predetermined number of cycles, and means for controlling pacemaker rate as a function of said QT indicated rate when said absence is determined.

3. The pacemaker as described in claim 1, wherein said sensed atrial signals are P wave, and comprising P wave analysis means for analyzing sensed P wave signals and determining whether they meet predetermined logical conditions, said control means controlling pacemaker timing in accordance with said indicated rate when said P waves do not meet said predetermined logical conditions.

4. The pacemaker as described in claim 1, comprising means for adjusting the pacemaker rate as a sensitivity function of determined QT interval, and means for adjusting said sensitivity function as a function of sensed atrial rate.

5. The pacemaker as described in claim 1, comprising means for operating said pacemaker in dual chamber synchronous mode operation, atrial means for determining when the natural sinus rhythm as reflected in sensed atrial signals disappears, said control means comprising alternate control means for controlling the pacing rate in an indicated rate mode as a function of said indicated rate when said sinus rhythm is found to have disappeared.

6. The dual chamber pacemaker as described in claim 5, comprising means for testing for when said atrial signals reappear, and returning means for returning said pacemaker from said indicated rate mode to synchronous mode operation when said atrial signals reappear.

7. The pacemaker as described in claim 6, wherein said control means comprises means for transferring control from said synchronous mode to said indicated rate mode only when a plurality of atrial signals have been analyzed.

8. The pacemaker as described in claim 1, further comprising parameter sensing means for at least one body parameter, and means for controlling the pacing rate of said pacemaker in a sensor mode as a function of the output of said parameter sensing means.

9. The pacemaker as described in claim 1, comprising atrial stimulus means for delivering periodic atrial stimulus pulses at a determined atrial pacing rate, and means for setting said atrial pacing rate as a function of said determined QT interval.

10. Dual chamber pacemaker apparatus having synchronous means for operating in a synchronous mode of operation, said synchronous means including atrial sensing means for sensing atrial signals and atrial control means for controlling the ventricular pacing rate in an atrial rate control mode, and alternate means for operating in at least one alternate ventricular rate control mode, logic means for performing logical tests on said atrial signals and for deciding whether to maintain said atrial rate control mode as a function of said logical tests, and rate mode means for controlling the pacemaker rate control mode as a function of said logical decision.

11. The dual chamber pacemaker apparatus as described in claim 10, wherein said alternate means comprises additional rate determining means having QT means for determining the QT interval following delivered ventricular stimulus pulses.

12. The dual chamber pacemaker apparatus as described in claim 10, wherein said alternate means comprises body sensing means for sensing a non-cardiac body parameter.

13. The dual chamber pacemaker apparatus as described in claim 11, wherein said alternate means further comprises body sensing means for sensing a non-cardiac body parameter.

14. The dual chamber pacemaker apparatus as described in claim 10, further comprising atrial rate means for determining the rate of said sensed atrial signals, and wherein said alternate means comprises additional rate determining means and said logic means comprises means for comparing the rate of sensed atrial signals with the rate determined by said alternate means.

15. The dual chamber pacemaker as described in claim 10, wherein said atrial control means comprises means for tracking the atrial rate when natural atrial signals are occurring, and for gradually changing the ventricular pacing rate upon transferring from atrial rate control to said alternate rate control.

16. Dual chamber pacemaker apparatus with means for pacing and sensing in both the atrium and the ventricle, comprising
   atrial rate control means for controlling pacing rate as a function of sensed atrial signals,
   alternate rate control means for alternate controlling of said pacing rate, said alternate rate control means having information means for determining patient information and for determining an alternate heartbeat rate as a function of said patient information,
   tracking means for tracking said pacing rate,
   logic means for comparing said atrial controlled rate with said alternate heartbeat rate and for determining when the pacing rate is to be atrial controlled and when alternate controlled, and
   rate control means for switching rate control from one of said atrial control and said alternate control to the other, and for effecting gradual change of said pacing rate from said tracked rate to the controlled rate following switching of rate control.

17. The dual chamber pacemaker apparatus as described in claim 16, comprising means for placing said apparatus in DVI operation when rate control is switched from atrial to alternate.

18. The dual chamber pacemaker apparatus as described in claim 16, wherein said alternate rate control means comprises means for adjusting rate as a function of Q-T interval.

19. The dual chamber pacemaker apparatus as described in claim 16, wherein said alternate rate control means comprises body sensor means for deriving body information from at least one source outside of the patient's heart.

20. The dual chamber pacemaker apparatus as described in claim 16, comprising synchronous mode means for operating said pacemaker apparatus in a synchronous mode of operation when in atrial rate control.

21. The dual chamber pacemaker apparatus as described in claim 20, comprising means for overdriving the spontaneous ventricular heartbeat and pacing the ventricle, and Q-T means for determining a desired pacing rate as a function of sensed Q-T interval.

* * * * *